United States Patent [19]

Murrell et al.

[11] Patent Number: 4,795,633

[45] Date of Patent: Jan. 3, 1989

[54] VACCINE FOR SWINE TRICHINOSIS

[75] Inventors: Kenneth D. Murrell, Rockville; Howard R. Gamble, Bowie, both of Md.; Hanspeter Marti, Basel, Switzerland

[73] Assignee: The United States of America as represented by the Secretary of Agriculture, Washington, D.C.

[21] Appl. No.: 68,499

[22] Filed: Jul. 1, 1987

[51] Int. Cl.[4] .................... A61K 39/002; A61K 39/00
[52] U.S. Cl. ....................................... 424/88; 424/92; 435/947
[58] Field of Search .................... 424/88, 92; 425/947

[56] References Cited

U.S. PATENT DOCUMENTS

| | | | |
|---|---|---|---|
| 4,152,414 | 5/1979 | Harris et al. | 424/92 X |
| 4,152,415 | 5/1979 | Harris et al. | 424/92 X |
| 4,469,672 | 9/1984 | Harris et al. | 424/92 X |

OTHER PUBLICATIONS

D. D. Despommier, "Partial Purification and Characterization of Protection-Inducing Antigens from the Muscle Larva of *Trichinella spiralis* by Molecular Sizing Chromatography and Preparative Flatbed Isoelectric Focusing," Parasit. Immunol. 3:261–272 (1981).
H. R. Gamble, "Comparison of Immune Effects in Mice Immunized with *Trichinella spiralis* Adult and Larval Antigens," J. Parasit. 71:680–682 (1985).
H. R. Gamble, "*Trichinella spiralis:* Immunization of Mice Using Monoclonal Antibody Affinity-Isolated Antigens," Exp. Parasitol, 59:398–404 (1985).
D. S. Silberstein et al., "Immunization with Purified Antigens Protects Mice from Lethal Infection with *Trichinella spiralis*," J. Parasit. 71:516–517 (1985).
D. S. Silberstein et al., "Effects on *Trichinella spiralis* of Host Responses to Purified Antigens," Science 227:948–950 (1985).
K. D. Murrell et al., "Immunization of Swine Against *Trichinella spiralis*," Vet. Parasitol, 15:263–270 (1984).
H. R. Gamble et al., "Inoculation of Pigs Against *Trichinella spiralis* Using Larval Excretory-Secretory Antigens," Am. J. Vet. Res. 47:2396–2399 (1986).
M. Philipp et al., "Immune Response to Stage-Specific Surface Antigens of the Parasitic Nematode *Trichinella spiralis*," J. Exp. Med. 154:210–215 (1981).
M. Jungery et al., "A Major Change in Surface Antigens During the Maturation of Newborn Larvae *Trichinella spiralis*," Mol. Biochem. Parasitol. 7:101–109 (1983).
G. Ortega-Pierres et al., "Protection Against *Trichinella spiralis* Induced by a Monoclonal Antibody that Promotes Killing of Newborn Larvae by Granlocytes," Parasit. Immunol. 6:275–284 (1984).
D. D. Despommier, "Immunogenicity of the Newborn Larva of *Trichinella Spiralis*," J. Parasitol. 57:531–534 (1971).
E. R. James et al., "Immunity to *Trichinella spiralis*. VII. Resistance Stimulated by the Parenteral Stages of the Infection," J. Parasitol. 63:720–723 (1977).
R. G. Bell et al., "*Trichinella spiralis:* Nonspecific Resistance and Immunity to Newborn Larvae In Inbred Mice," Exp. Parasitol. 60:101–110 (1985).

*Primary Examiner*—Howard E. Schain
*Attorney, Agent, or Firm*—M. Howard Silverstein; David G. McConnell; Beverly K. Johnson

[57] ABSTRACT

A vaccine for immunization of swine against *Trichinella spiralis* "*T. spiralis*" wherein the immunogenic substance is inert newborn larvae of *T. spiralis* emulsified with a suitable adjuvant. The vaccine induces greater than 60% immunity in swine and offers a novel approach to the control of swine trichinosis. Preferably, the inert newborn larvae preparation is emulsified with Freund's complete adjuvant.

8 Claims, 3 Drawing Sheets

VACCINE FOR SWINE TRICHINOSIS

BACKGROUND OF THE INVENTION

1. Field of the Invention

This invention relates to a vaccine for immunization against swine trichinosis. More particularly, this invention relates to a novel vaccine for swine trichinosis wherein the immunogenic substance is an antigen preparation of inert newborn larvae of *Trichinella spiralis* ("*T. spiralis*").

2. Description of the Prior Art

Current strategies for controlling *T. spiralis*, the causative agent of trichinosis in swine, include antemortem and postmortem inspection and meat processing including curing, freezing and cooking. Yet, *T. spiralis* continues to cause the pork industry more than four hundred million dollars per year. Consequently, there exists a need for a more effective approach to the control of this parasite.

One such approach recognized in the prior art is the development of a vaccine for immunization against *T. spiralis*. Research on the antigens of this parasite has been encouraged toward this effort. For example, stichosome antigens derived from the muscle larvae and extracts of adult stages has been reported to be moderately effective in inducing immunity. D. D. Despommier [Parasit. Immunol. 3: 261-272 (1982)]; H. R. Gamble [J. Parasit. 71: 680-682 (1985)]. Isolation and characterization of stichosome antigens by immunoaffinity purification with monoclonal antibodies has also been achieved. H. R. Gamble [Exp. Parasitol. 59: 398-404 (1985)]; D. S. Silberstein et al. [J. Parasit. 71: 516-517 (1985)]; D. S. Silberstein et al. [Science 227: 948-950 (1985)]. However, these antigens have only been moderately protective in swine immunization trials. K. D. Murrell et al. [Vet. Parasitol. 15: 263-270 (1984)]; H. R. Gamble et al. [Am. J. Vet. Res. 47: 2396-2399 (1986)].

It has also been shown that the surface of the newborn larvae of *T. spiralis* is antigenically diverse and stage specific, M. Philipp et al. [J. Exp. Med. 154: 210-215 (1981)]; M. Jungery et al. [Mol Biochem. Parasitol. 7: 101-109 (1983)], and that significant changes in the antigenic complexity of the newborn larvae surface occurs during its maturation. G. Ortega-Pierres et al. [Parasit. et al. Immunol. 6: 275-284 (1984)]. Further, antibodies to viable newborn larvae of *T. spiralis* have been shown to passively transfer protective immune response in rodents. D. D. Despommier [J. Parasitol. 57: 531-534 (1971)]. However, freeze-thaw killed newborn larvae were not effective in inducing aquired immunity in rodents. D. D. Despommier, Ibid.

The results of prior research does suggest the prospect of producing a vaccine against *T. spiralis*. However, until now there has been no vaccine which induces a significant level of immune response against *T. spiralis* in swine.

SUMMARY OF THE INVENTION

We have now developed a vaccine which unexpectedly produces greater than 60% protective immunity in swine against *T. spiralis*. The vaccine comprises inert newborn larvae of *T. spiralis* emulsified with a suitable adjuvant. The vaccine provides a method for immunizing swine against *T. spiralis* by inoculating the animal with an effective immunizing amount of the invention vaccine.

Accordingly, it is an object of this invention to provide a vaccine for swine trichinosis which produces a high level of protective immunity in swine.

Another object of this invention is to provide a method of immunizing swine against trichinosis through vaccination.

DETAILED DESCRIPTION OF THE INVENTION

Figure 1:
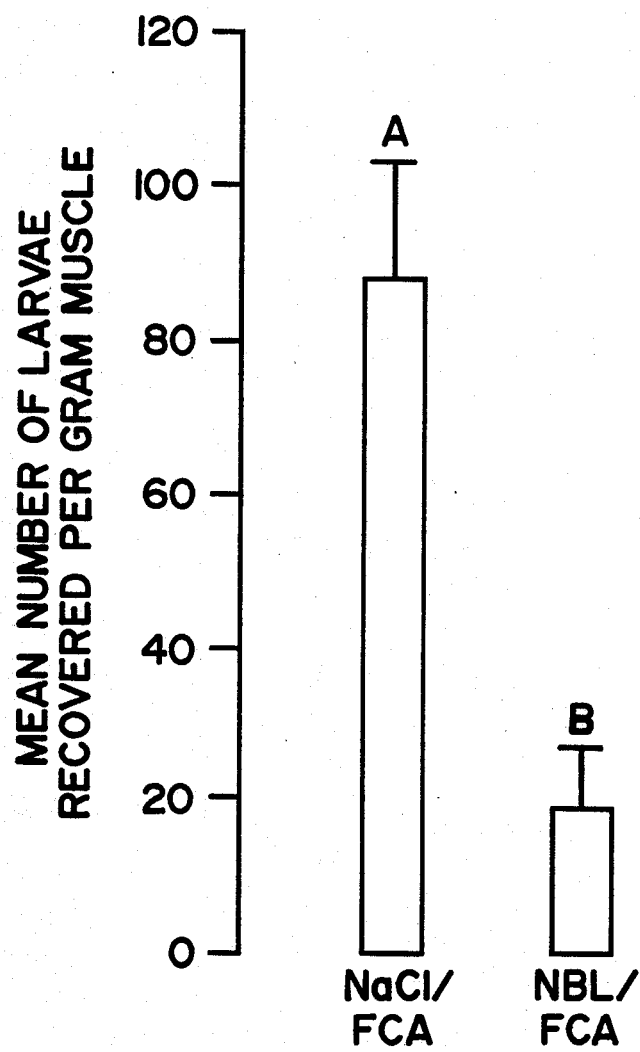
FIG. 1 shows the means number of muscle larvae recovered, after challenge, from pigs immunized with *T. spiralis* whole newborn larvae (NBL/FCA) and saline controls (NaCl/FCA).
Figure 2:
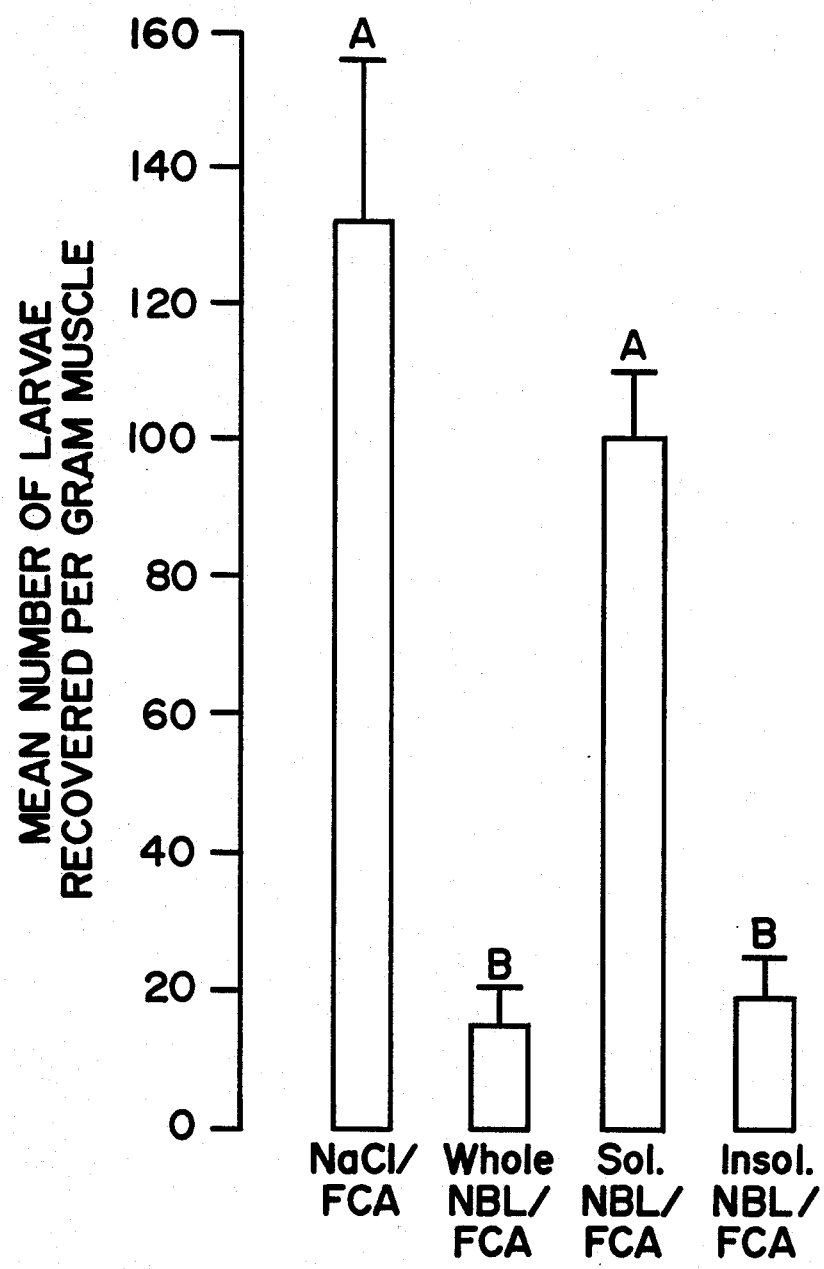
FIG. 2 shows the mean number of muscle larvae recovered, after challenge, from pigs immunized with *T. spiralis* whole newborn larvae, the soluble (Sol. NBL/FCA) and insoluble (Insol. NBL/FCA) fractions produced from the centrifiguation of whole newborn larvae, and saline controls.
Figure 3:
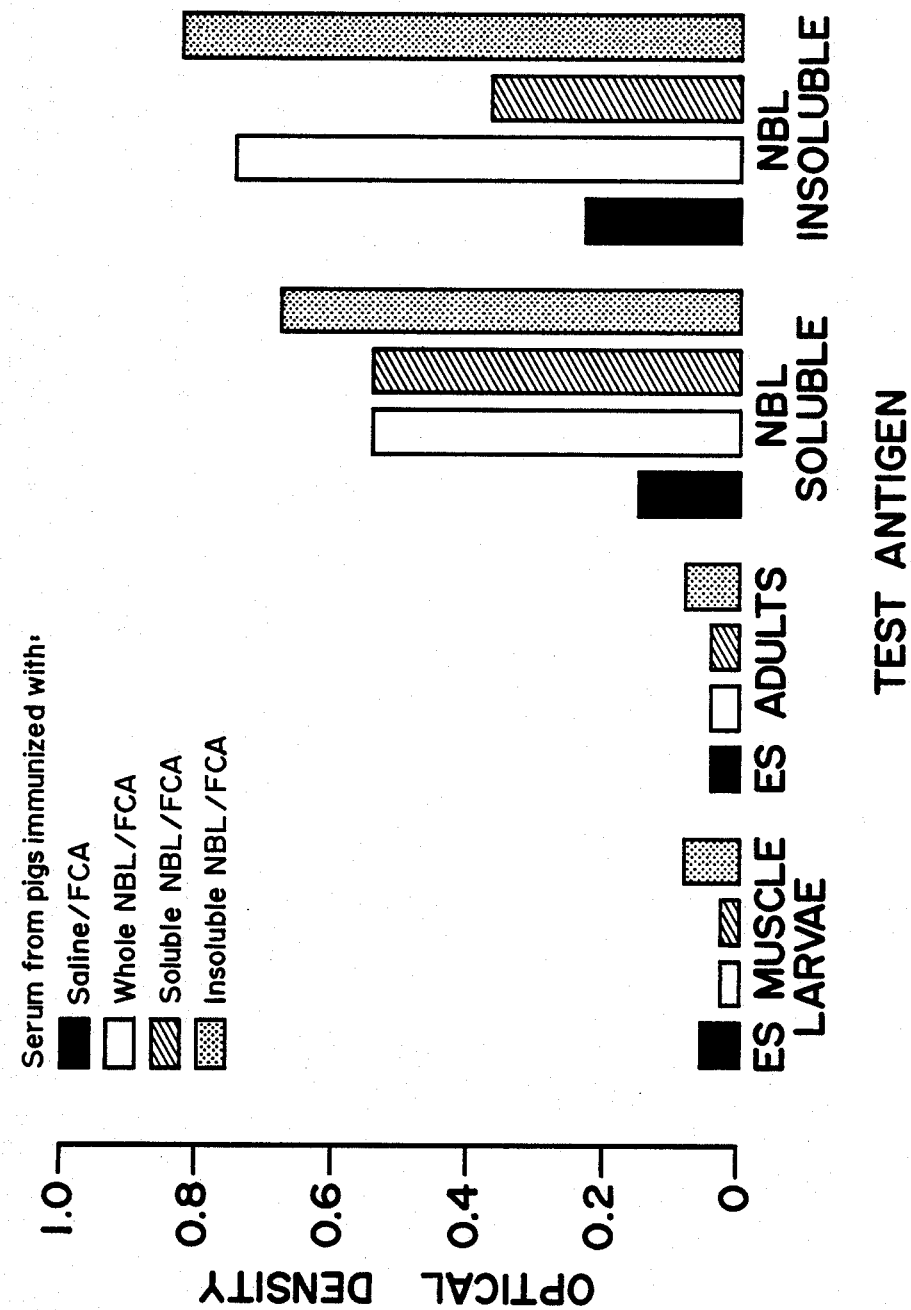
FIG. 3 shows the results of enzyme-linked immunosorbent antibody assay for antibody in immunized and control pigs using various *T. spiralis* antigen preparations.

For purposes of the invention, the term "newborn larvae" is used herein to designate the first stage embryonic larvae produced by adult female *T. spiralis* prior to maturation and differentiation. The term "inert" is used herein to mean non-living newborn larvae of *T. spiralis*.

*T. spiralis* was maintained in female Sprague Dawley rats by serial passage. Muscle larvae "L1" were recovered by digestion, in 1:1 ratio pepsin-HCl (1% each), of eviscerated, ground rat carcasses and washed by settling through several cycles in warm water. Adult worms were recovered from intestines of rats six days post inoculation with infective L1. Recovery was accomplished using a modified Baermann apparatus with Hank's balanced salt solution at 37° C.

Adult female worms were incubated in Dulbecco's modified Eagle's medium (DMEM) supplemented with penicillin (250 units/ml), streptomycin (250 μg/ml), 2 mM glutamine, 1 mM Na-pyruvate, and 10 mM Hepes at 37° C. in 10% $CO_2$. Newborn larvae were harvested after 24 hours by passage through a 44 μm mesh screen. Next, the larvae was washed in saline, centrifuged and frozen at −70° C. until further processing. The culture fluid supernatant containing the excretory secretory ("ES") adult antigens may also be recovered, concentrated by filtration and stored at −70° C.

For use in pig immunization trials, frozen newborn larvae were thawed from −70° C. in a 37° C. water bath. Thereafter, the larvae was quick frozen in liquid nitrogen and thawed again at room temperature. Where soluble newborn larvae fractions and insoluble newborn larvae fractions were prepared, the thawed whole newborn larvae were disrupted by sonication following the quick freeze-thaw process, and separated in soluble and insoluble fractions by centrifugation using a Eppendorf microfuge. For purposes of the invention, the term "soluble newborn larval fraction" is used herein to designate the supernatant resulting from sonication and centrifugation of freeze-thawed whole newborn larvae. The term "insoluble newborn larval fraction" is used herein to designate the insoluble portion resulting from sonication and centrifugation of the freeze-thawed whole newborn larvae.

Whole freeze-thawed newborn larvae and soluble and insoluble newborn larval fractions were emulsified in Freund's complete adjuvant (FCA) to prepare the vaccine of the invention. Although FCA is the preferred adjuvant, it is within the compass of this invention to use any known adjuvant or emulsifier, e.g. aluminum hydroxide, to prepare the invention vaccine provided that the adjuvant does not significantly interfere with the effectiveness of the vaccine.

IMMUNIZATION OF PIGS

Groups of pigs were immunized in two trials, Trial 1 and Trial II, using the vaccine preparation of the invention.

The pigs used in each of the two trials were mixed breeds, male and female, from Hamshire x (Yorkshire x Duroc) dams and purebred Yorkshire or Duroc sires. Care was taken to distribute pigs evenly by size in each trial.

The vaccine of the invention was administered in 3 doses of antigen given intraperitoneally in a 1:1 volume ratio emulsion in FCA at weekly intervals. In Trial I, whole freeze-thawed newborn larvae were administered at $3.5\times10^5$ newborn larvae/dose/pig. In Trial II, either of whole newborn larvae, soluble newborn larval fractions and insoluble newborn larval fractions were given at $5\times10^5$ newborn larvae/dose/pig. Control groups of pigs in each of Trial I and II were injected with saline in FCA.

In both trials, pigs were challenged with 2000 infective L1 of *T. spiralis* one week after the last immunization. Six weeks after challenge, the pigs were killed, their tongue and diaphragm were digested, and worms were recovered therefrom. The number of L1 recovered was determined and expressed as larvae per gram of tissue. Statistical analysis of the L1 recovered for each of Trial I and Trial II is shown using Duncan's multiple range test (DMRT) in FIGS. 1 and 2, respectively. Ranking in DMRT is indicated by letters - groups with the same letter are not significantly different ($\alpha=0.05$).

As shown in FIG. 1, pigs immunized in Trial I with whole *T. spiralis* newborn larvae preparation yielded significantly fewer L1 after challenge than did the saline controls. In Trial II, the strongest response occurred in pigs receiving whole newborn larvae and the insoluble newborn larvae. As shown in FIG. 2, reductions in L1 recovery from pigs immunized with whole newborn larvae and the insoluble fraction of newborn larvae were 88.2 percent and 85.5 percent, respectively, as compared to the saline controls. Pigs immunized with the soluble newborn larval fraction did not express a significant resistance to challenge.

Blood samples taken after the last immunization but prior to the challenge infection were analyzed by triple antibody enzyme-linked immunosorbent assay (ELISA) at a serum dilution of 1:20 in ELISA washing buffer. L1 ES antigens, ES antigens of adult worms, and the soluble and insoluble newborn larval fractions were used. As shown in FIG. 3, pigs receiving newborn larval antigens had, prior to challenge, antibodies that reacted with both newborn larvae soluble and insoluble fractions. The ES antigens of the adult and L1 stages did not cross-react with antibodies induced in the newborn larval immunized swine.

It is understood that modification and variation may be made to the foregoing disclosure without departing from the spirit and scope of the invention.

We claim:

1. A vaccine for immunizing swing against *Trichinella spiralis* comprising an effective immunizing amount of inert newborn larvae of *Trichinella spiralis* emulsified with an adjuvant.

2. The vaccine of claim 1 wherein the adjuvant is aluminum hydroxide.

3. The vaccine of claim 1 wherein the inert newborn larvae is freeze-thawed newborn larvae of *Trichinella spiralis*.

4. The vaccine of claim 1 wherein the adjuvant is Freund's complete adjuvant.

5. The method for immunizing swing against *Trichinella spiralis* comprising inoculating the animal with an effective immunizing amount of inert newborn larvae of *Trichinella spiralis* emulsified with a adjuvant.

6. The method of claim 5 wherein the inert newborn larvae is freeze-thawed newborn larvae of *Trichinella spiralis*.

7. The method of claim 5 wherein the adjuvant is Freund's complete adjuvant.

8. The method of claim 5 wherein the adjuvant is aluminum hydroxide

* * * * *